(12) United States Patent
Canady et al.

(10) Patent No.: US 11,464,558 B2
(45) Date of Patent: Oct. 11, 2022

(54) PLASMA ACCESSORY

(71) Applicant: U.S. Patent Innovations LLC, Takoma Park, MD (US)

(72) Inventors: Jerome Canady, Lakeland, FL (US); Taisen Zhuang, Rockville, MD (US)

(73) Assignee: U.S. Patent Innovations LLC, Takoma Park, MD (US)

( * ) Notice: Subject to any disclaimer, the term of this patent is extended or adjusted under 35 U.S.C. 154(b) by 301 days.

(21) Appl. No.: 16/550,631

(22) Filed: Aug. 26, 2019

(65) Prior Publication Data
US 2019/0380764 A1 Dec. 19, 2019

Related U.S. Application Data

(63) Continuation of application No. 14/876,358, filed on Oct. 6, 2015, now Pat. No. 10,405,913.
(Continued)

(51) Int. Cl.
*H05H 1/00* (2006.01)
*A61B 18/04* (2006.01)
(Continued)

(52) U.S. Cl.
CPC .............. *A61B 18/042* (2013.01); *H05H 1/46* (2013.01); *A61B 2018/00083* (2013.01);
(Continued)

(58) Field of Classification Search
CPC ........ A61B 18/042; A61B 2018/00083; A61B 2018/00178; A61B 2018/00601; H05H 1/46
See application file for complete search history.

(56) References Cited

U.S. PATENT DOCUMENTS 3,612,807 A 10/1971 Liefkens et al.
3,825,004 A * 7/1974 Durden, III ........ A61B 18/1402
604/20
(Continued)

FOREIGN PATENT DOCUMENTS

WO 03028542 4/2003
WO 2012/061535 10/2012
WO 2012/167089 12/2012

OTHER PUBLICATIONS

E Stoffels, A J Flikweert, W W Stoffels and G M W Kroesen, "Plasma needle: a non-destructive atmospheric plasma source for fine surface treatment of (bio)materials," Plasma Sources Sci. Technol. 11 (2002) 383-388.

*Primary Examiner* — Daniel W Fowler
(74) *Attorney, Agent, or Firm* — 24IP Law Group USA, PLLC; Timothy DeWitt

(57) ABSTRACT

A cold plasma accessory having a hand piece having within in it flexible tubing, wiring, a PCB board connected to the wiring, and a conductive connector tube electrically connected to the PCB board, the conductive connector tube having an inner channel, a rigid tube extending from the distal end of the hand piece, and an electrode within the rigid tube. The electrode comprises a conductive connector having a contact surface contacting the conductive connector tube, a distal end surface facing away from the conductive connector tube, and a channel extending through a center of the conductive connector, the channel being fluidly connected to the flexible tubing, the distal end surface of the conductive connector being outside of the channel in the conductive connector, and a conductive wire connected to the distal end surface of the conductive connector.

7 Claims, 18 Drawing Sheets

Related U.S. Application Data

(60) Provisional application No. 62/060,525, filed on Oct. 6, 2014.

(51) Int. Cl.
  *H05H 1/46* (2006.01)
  *A61B 18/00* (2006.01)
  *H05H 1/24* (2006.01)

(52) U.S. Cl.
  CPC ............... *A61B 2018/00178* (2013.01); *A61B 2018/00601* (2013.01); *H05H 1/245* (2021.05); *H05H 2240/20* (2013.01); *H05H 2245/30* (2021.05)

(56) References Cited

U.S. PATENT DOCUMENTS

| | | | |
|---|---|---|---|
| 3,903,891 A | | 9/1975 | Brayshaw |
| 3,938,525 A | * | 2/1976 | Goucher ............... A61B 18/042 606/27 |
| 4,040,426 A | | 8/1977 | Morrison |
| 4,057,064 A | | 11/1977 | Morrison et al. |
| 4,232,676 A | | 11/1980 | Herczog |
| 4,682,596 A | | 7/1987 | Bales et al. |
| RE33,925 E | | 5/1992 | Bales et al. |
| 5,233,155 A | | 8/1993 | Frind |
| 5,242,442 A | * | 9/1993 | Hirschfeld ......... A61B 18/1402 604/35 |
| 5,605,539 A | * | 2/1997 | Buelna ............... A61B 18/1482 604/21 |
| 5,720,745 A | | 2/1998 | Farin et al. |
| 5,935,124 A | | 8/1999 | Klumb et al. |
| 6,165,164 A | | 12/2000 | Hill et al. |
| 6,679,882 B1 | | 1/2004 | Kornerup |
| 2001/0034519 A1 | | 10/2001 | Goble et al. |
| 2003/0004506 A1 | | 1/2003 | Messing |
| 2003/0088247 A1 | * | 5/2003 | Ineson ............... A61B 18/1402 606/42 |
| 2005/0240177 A1 | * | 10/2005 | Tabermejo, Jr. ... A61B 18/1442 606/42 |
| 2006/0052774 A1 | * | 3/2006 | Garrison ............... A61B 18/042 606/42 |
| 2007/0029500 A1 | | 2/2007 | Coulombe |
| 2007/0049927 A1 | * | 3/2007 | Saltzman ........... A61B 18/1402 606/45 |
| 2009/0065485 A1 | | 3/2009 | O'Neill et al. |
| 2011/0077642 A1 | | 3/2011 | Farin |
| 2011/0112528 A1 | | 5/2011 | Stieber et al. |
| 2012/0187841 A1 | | 7/2012 | Kindel et al. |
| 2012/0283732 A1 | | 11/2012 | Lam |
| 2014/0378892 A1 | | 12/2014 | Keidar |

* cited by examiner

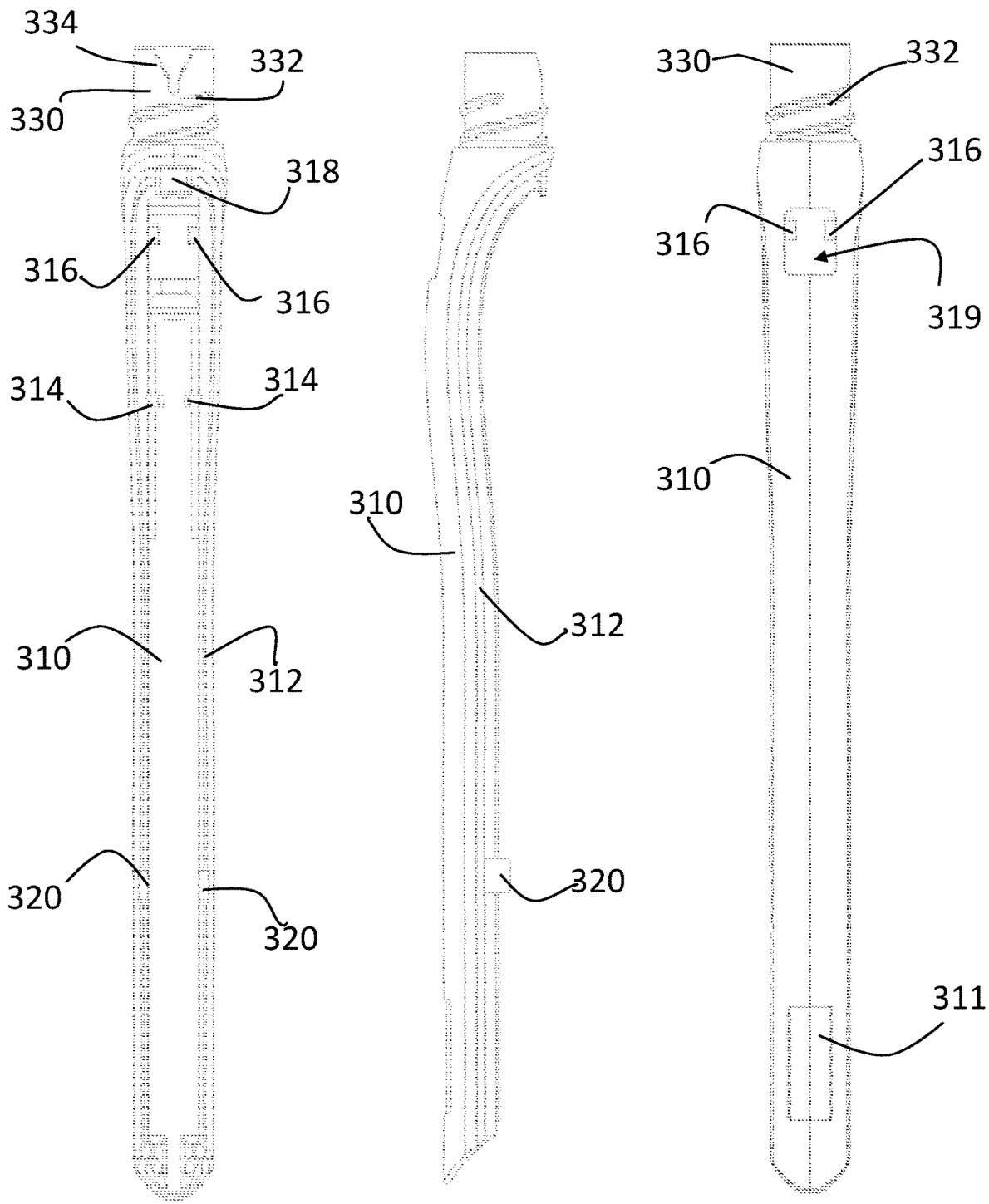

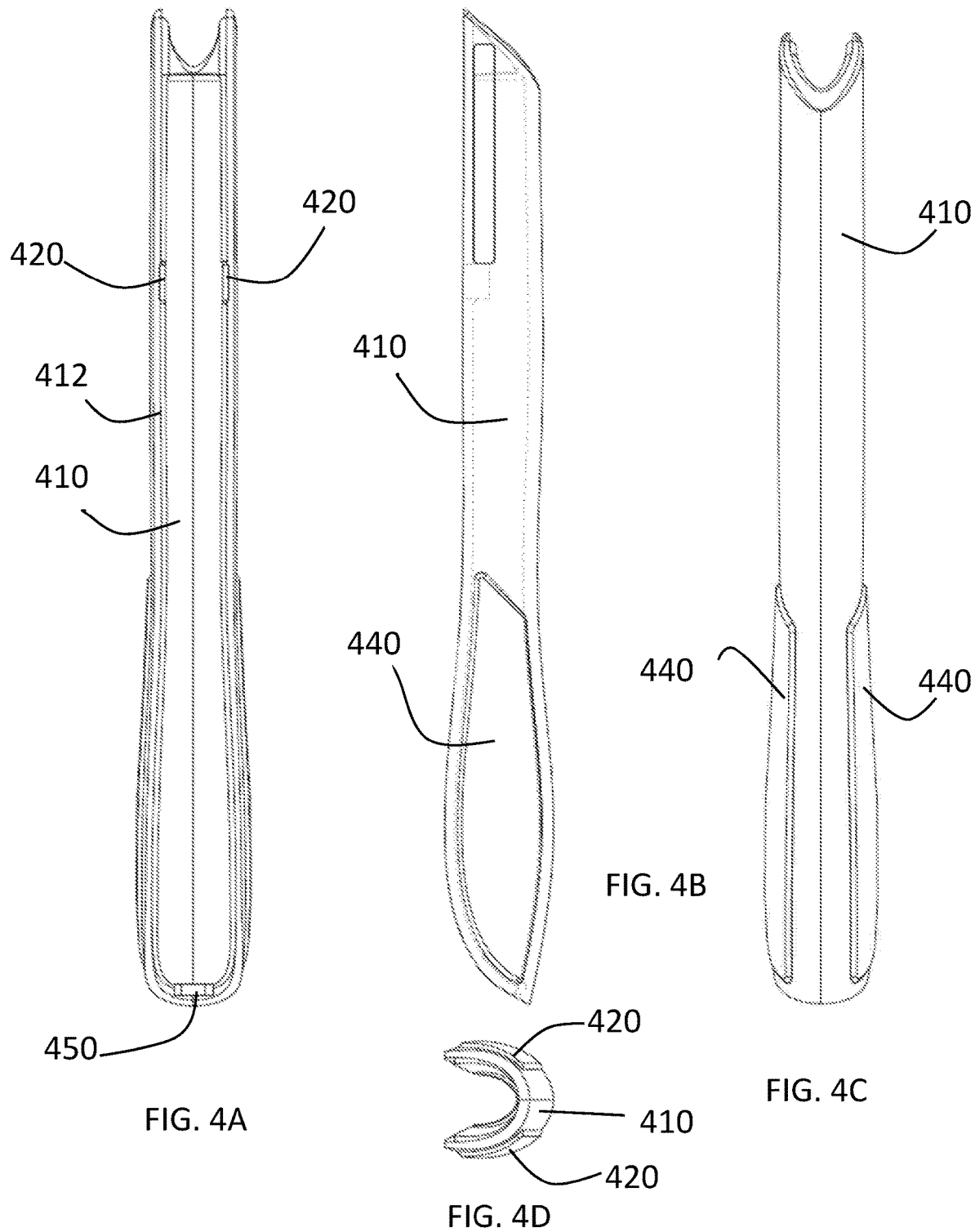

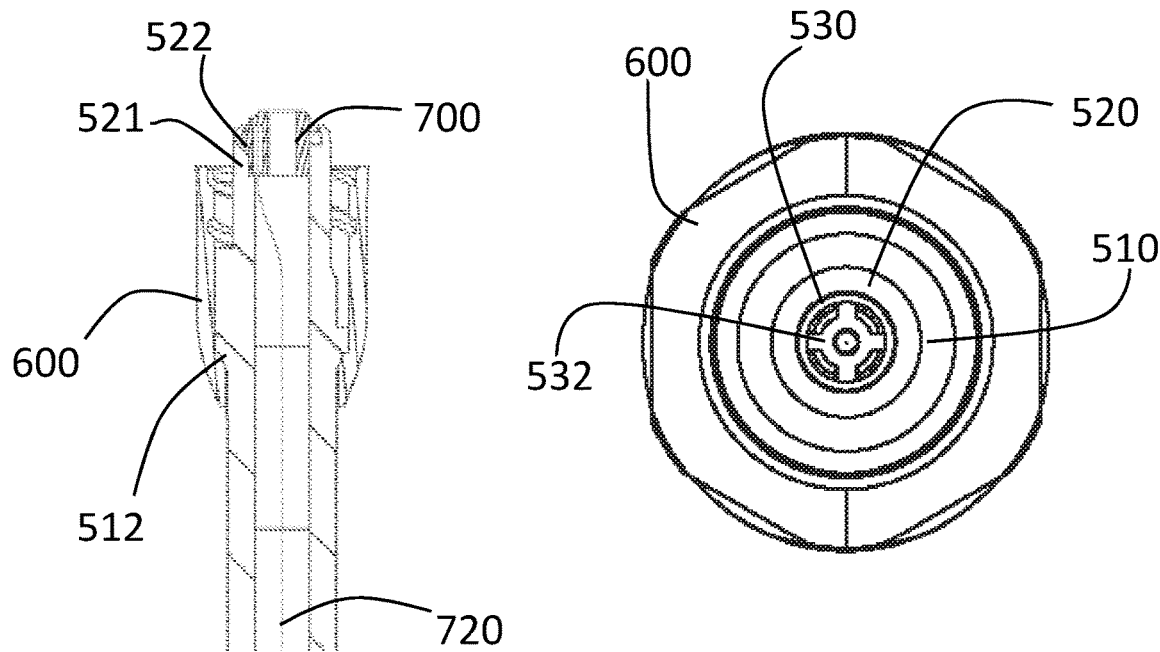
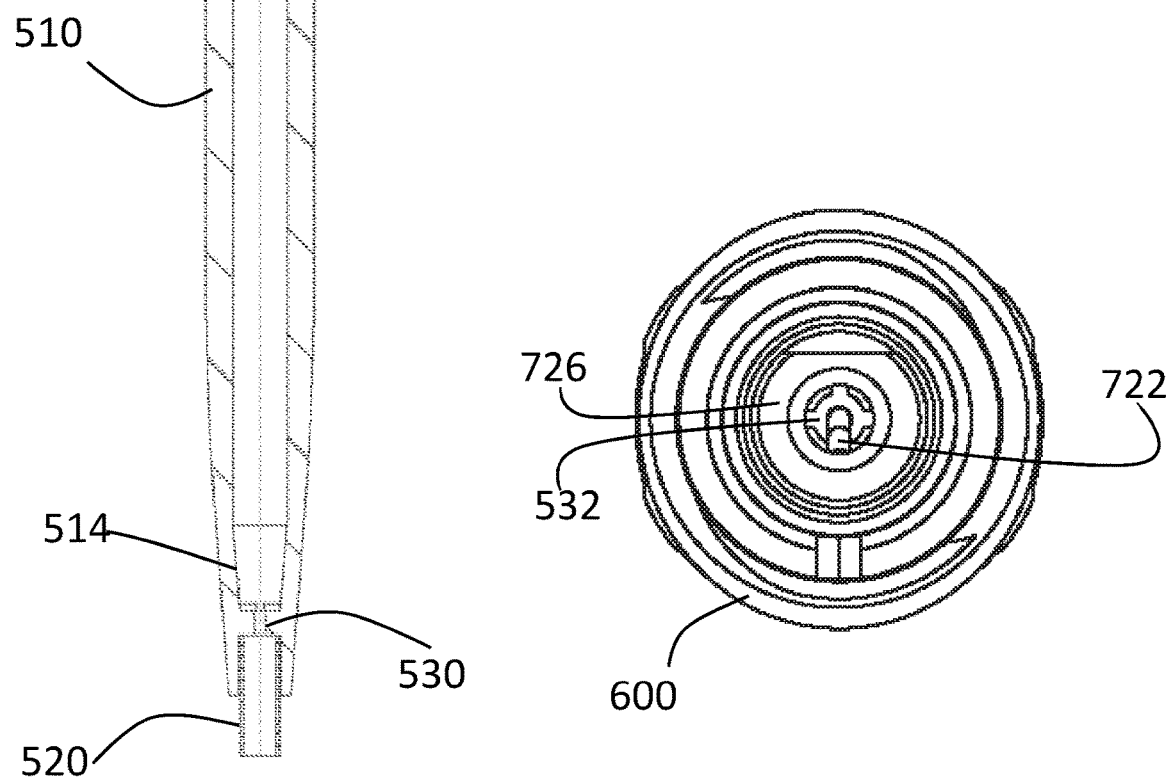
FIG. 5D
FIG. 5E
FIG. 5F

600

610

612

620

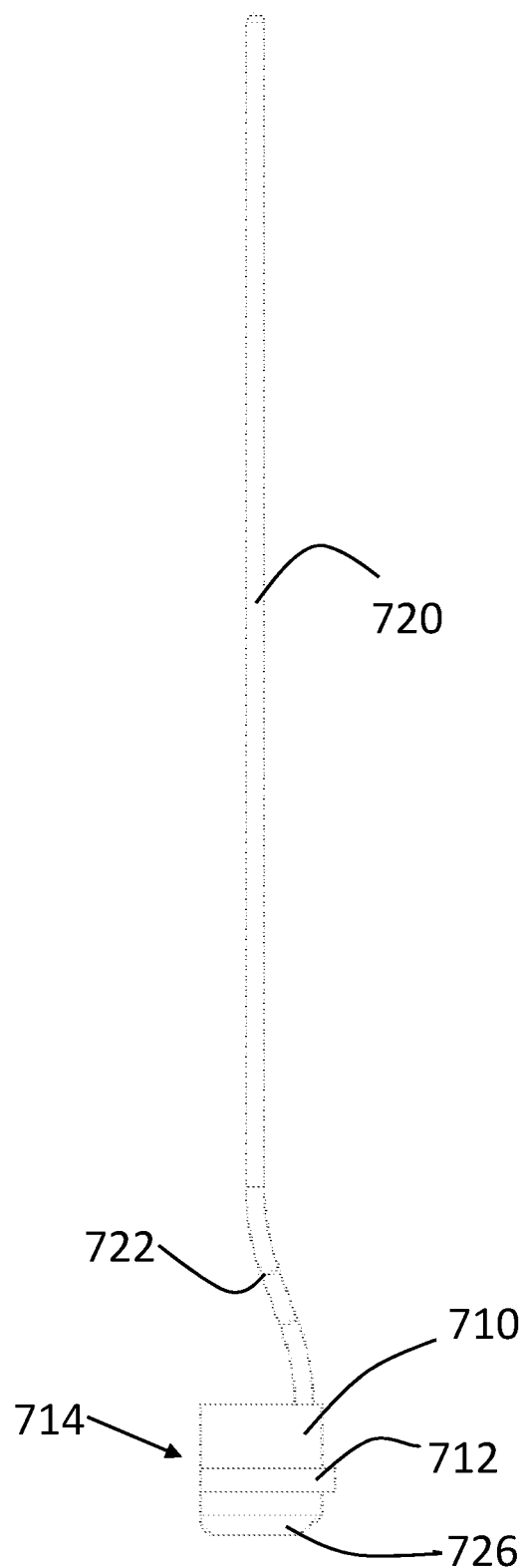
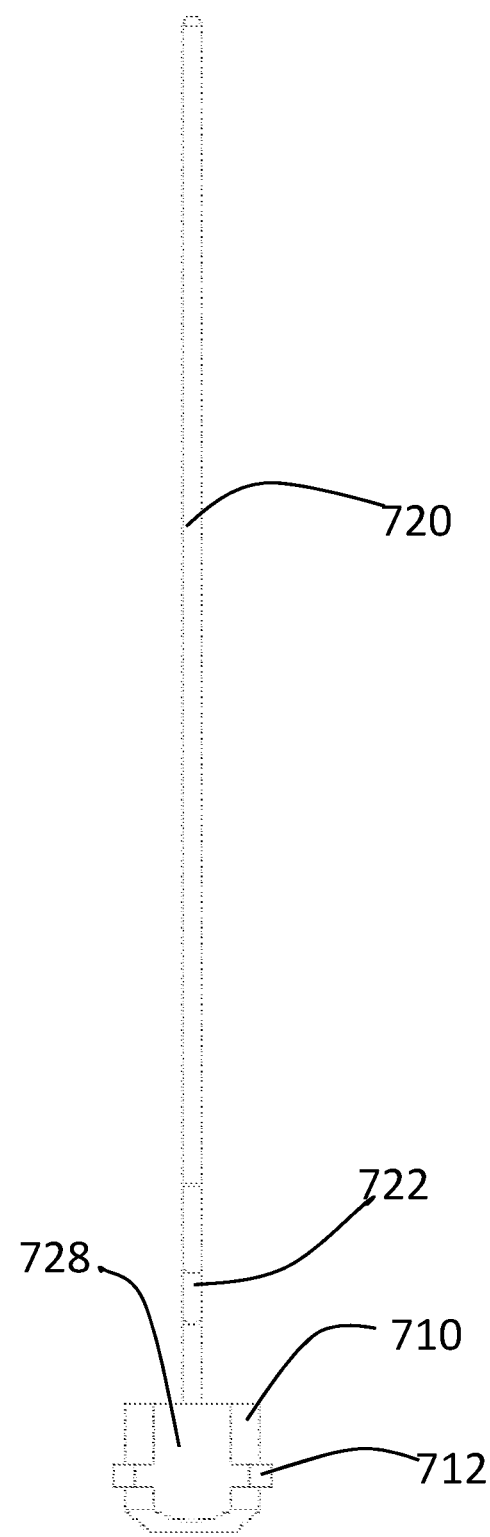
FIG. 7C                    FIG. 7D

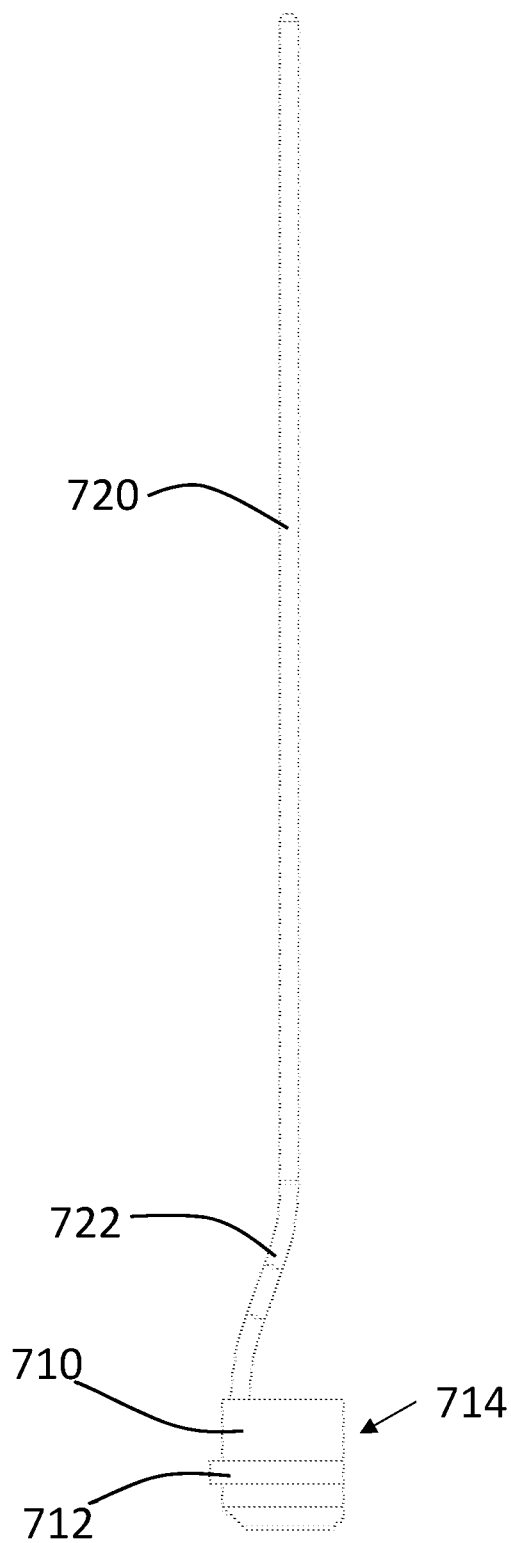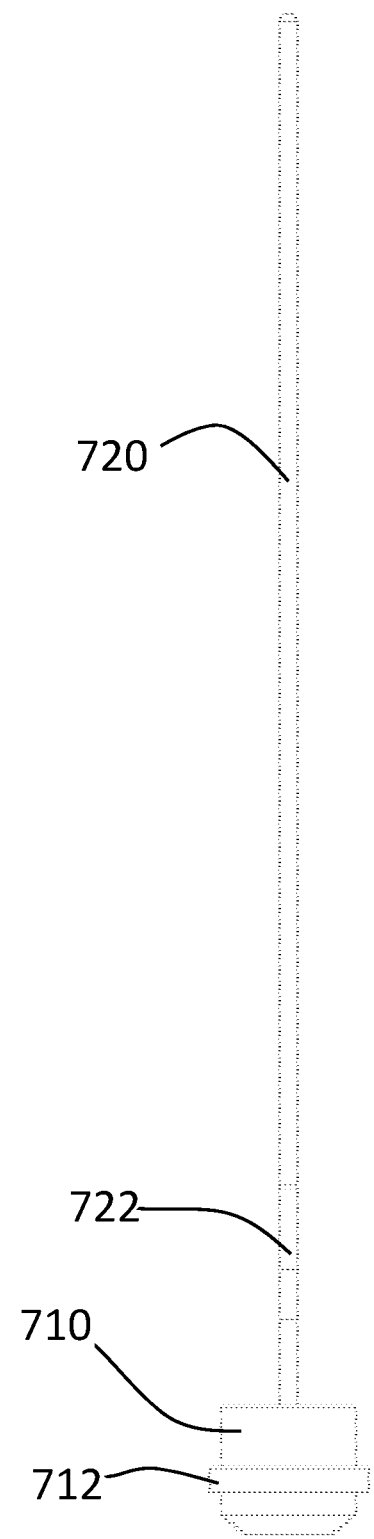
FIG. 7E
FIG. 7F

PLASMA ACCESSORY

CROSS-REFERENCE TO RELATED APPLICATIONS

The present application is a continuation of U.S. patent application Ser. No. 14/876,358, filed Oct. 6, 2015, which claims the benefit of the filing of U.S. Provisional Patent Application Ser. No. 62/060,525 entitled "Cold Plasma Scalpel" filed on Oct. 6, 2014.

The aforementioned applications are hereby incorporated by reference in their entirety.

STATEMENT REGARDING FEDERALLY SPONSORED RESEARCH OR DEVELOPMENT

None.

BACKGROUND OF THE INVENTION

Field of the Invention

The present invention relates to electrosurgical systems and methods, and more particularly, to a cold plasma scalpel.

Brief Description of the Related Art

Plasma is an ionized gas that is typically generated in high-temperature laboratory conditions. Recent progress in atmospheric plasmas has led to the creation of cold plasmas with ion temperature close to room temperature. Earlier studies demonstrated the non-aggressive nature of the cold plasma. After it was shown, albeit indirectly, that plasma can interact with organic materials without causing thermal/electric damage to the cell surface, several biological applications were examined. Low-temperature or cold plasmas have an increasing role to play in biomedical applications. The potential use in biomedical applications has driven the development of a variety of reliable and user-friendly plasma sources. There is still some controversy with respect to the mechanism of plasma-cell interaction. Some authors are of the opinion that ion species play the most important role in plasma-cell interactions by triggering intracellular biochemistry. Alternatively, others have suggested that neutral species play the primary role in some plasma-cell interaction pathways. Furthermore, the effects of various ion species may be highly selective; different species can have either "plasma killing" (such as O) or "plasma healing" (such as NO) effects. The role of other species, such as $O_3$ and OH, are not yet clear.

Even less clear has the nature of the interaction between cold plasmas and cancer tissue. Only limited research into the utility of cold plasma for cancer therapy has been performed. For the most part, these in-vitro studies are limited to skin cells and simple cellular responses to the cold plasma treatment. In addition, preliminary reports on plasma's in-vivo antitumor effect are reported. Recent studies have delineated cold plasma's effects on both the cellular and sub-cellular levels. On the cellular level, plasma effects include detachment of cells from the extracellular matrix and decreased migration velocity of cells. On the sub-cellular level, cell surface integrin expression is reduced. We examined the therapeutic potential of a cold plasma jet in cancer cell lines and tumors, focusing on selective tumor cell eradication capabilities and signaling pathway deregulation.

International Patent Application WO 2012/16708 disclosed a device that uses cold plasma to treat cancerous tumors. The device has a gas supply tube with a delivery end. The gas supply tube is configured to carry a gas to the delivery end. A syringe is provided having an opening. The syringe is connected to the supply tube and configured to carry the gas to the opening. A first electrode is positioned inside the syringe, and a second electrode is positioned adjacent to the opening. The first and second electrodes excite the gas to enter a cold plasma state prior to being discharged from the opening of the syringe. An endoscopic tube can be used instead of the syringe. An exhaust tube can be provided to remove gas introduced into the body cavity by the cold plasma jet.

International Patent Application WO 2012/061535 disclosed an electrosurgical method and device for simultaneously cutting and coagulating tissue with an electrosurgical device having an electrode and a channel wherein the channel has a port near a proximal end of the electrode, wherein the method comprises the steps of causing an inert gas to flow through the channel and exit the port, applying high-frequency energy to the electrode while the inert gas flows through the channel, wherein the high-frequency energy applied to the electrode continuously plasmatizes inert gas exiting the port, initiating an electrical discharge from the electrode through the continuously plasmatized inert gas to the tissue, cutting tissue with the electrode, maintaining the electrical discharge from the electrode through the plasmatized inert gas while cutting tissue with the electrode to cause coagulation of the tissue simultaneously with the cutting.

SUMMARY OF THE INVENTION

In a preferred embodiment, the present invention is an attachment for an electrosurgical hand piece. The attachment comprises a probe assembly having an elongated tube having a proximal end and a distal end, and an electrode. The electrode has at a proximal end a conductive connector, which has a proximal end, a distal end and a channel extending through the conductive connector. The conductive connector may be comprised of a nickel plated brass alloy. The electrode further has a conductive wire extending from the distal end of the conductive connector, the conductive wire being connected to the distal end of the conductive connector adjacent to the channel in the conductive connector. The conductive wire extends substantially along the length of the elongated tube and may or may not extend out of the end of the tube. The conduct wire may be comprised of tungsten. The attachment may further comprise an insulating tip at the distal end of the elongated tube; wherein the conductive wire extends at least partially through the insulating tip.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description or may be learned by practice of the invention.

BRIEF DESCRIPTION OF THE DRAWINGS

For a more complete understanding of the present invention and the advantages thereof, reference is now made to the following description and the accompanying drawings, in which:

FIG. 3D is a bottom view of a top hand piece portion of cold plasma scalpel hand piece in accordance with a preferred embodiment of the present invention FIG. 3E is a side view of a top hand piece portion of cold plasma scalpel hand piece in accordance with a preferred embodiment of the present invention FIG. 3F is a top view of a top hand piece portion of cold plasma scalpel hand piece in accordance with a preferred embodiment of the present invention FIG. 4A is a top view of a bottom hand piece portion of cold plasma scalpel hand piece in accordance with a preferred embodiment of the present invention.

FIG. 4B is a side view of a bottom hand piece portion of cold plasma scalpel hand piece in accordance with a preferred embodiment of the present invention.

FIG. 4C is a top view of a bottom hand piece portion of cold plasma scalpel hand piece in accordance with a preferred embodiment of the present invention.

FIG. 4D is a front perspective view of a bottom hand piece portion of cold plasma scalpel hand piece in accordance with a preferred embodiment of the present invention.

FIG. 5D is a cross-sectional view of a cold plasma scalpel in accordance with a preferred embodiment of the present invention.

FIG. 5E is a first end view of a cold plasma scalpel in accordance with a preferred embodiment of the present invention.

FIG. 5F is a second view of a cold plasma scalpel in accordance with a preferred embodiment of the present invention.

FIG. 7C is a first side view of an electrode of a cold plasma scalpel in accordance with a preferred embodiment of the present invention.

FIG. 7D is a top view of an electrode of a cold plasma scalpel in accordance with a preferred embodiment of the present invention.

FIG. 7E is a second side view of an electrode of a cold plasma scalpel in accordance with a preferred embodiment of the present invention.

FIG. 7F is a bottom view of an electrode of a cold plasma scalpel in accordance with a preferred embodiment of the present invention.

DETAILED DESCRIPTION OF THE PREFERRED EMBODIMENTS

Figure 1:
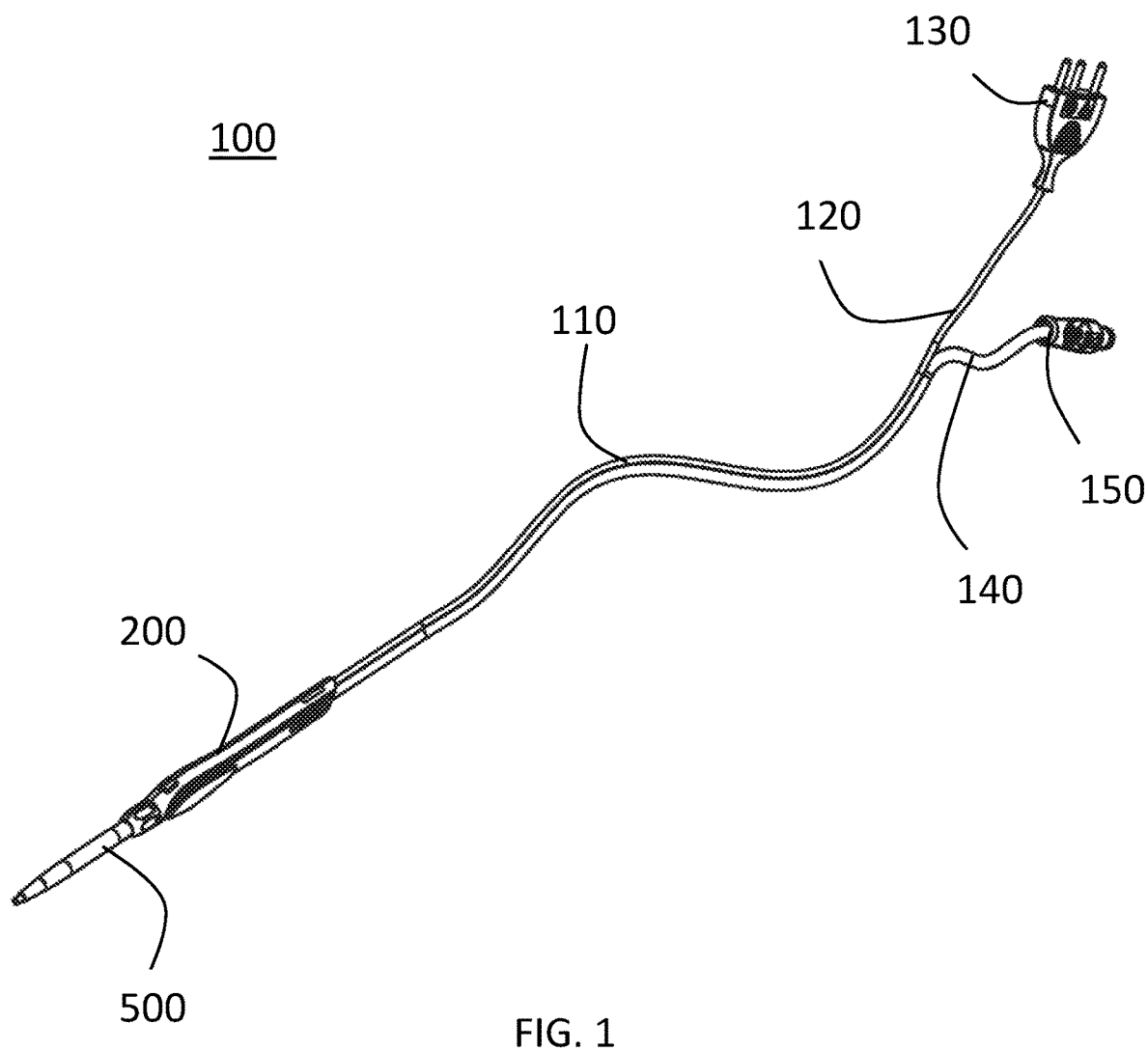
FIG. 1 is a perspective view of an electrosurgical accessory having a cold plasma scalpel in accordance with a preferred embodiment of the present invention.
Figure 2A:
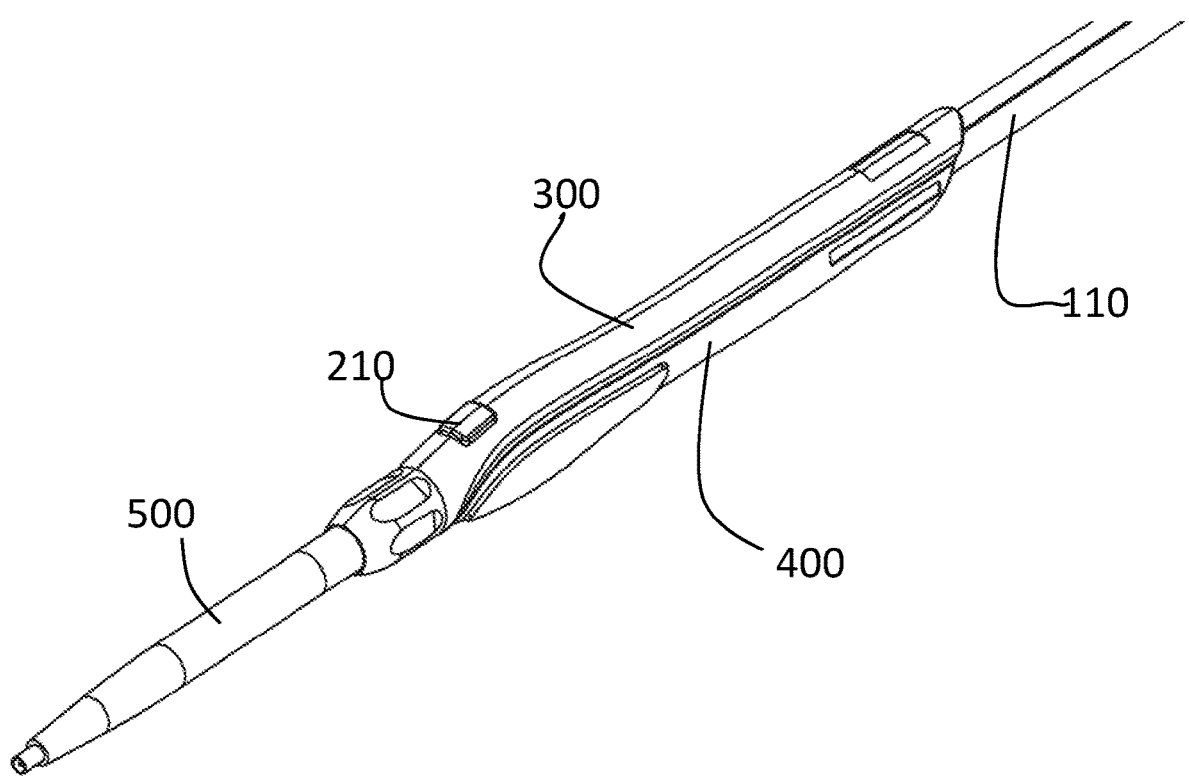
FIG. 2A is a perspective view of a cold plasma scalpel and electrosurgical hand piece in accordance with a preferred embodiment of the present invention.
Figure 2B:
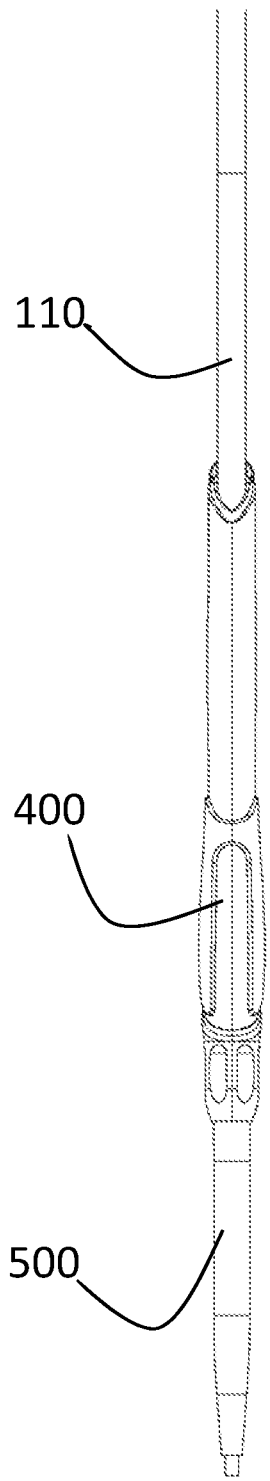
FIG. 2B is a bottom view of a cold plasma scalpel and electrosurgical hand piece in accordance with a preferred embodiment of the present invention.
Figure 2C:
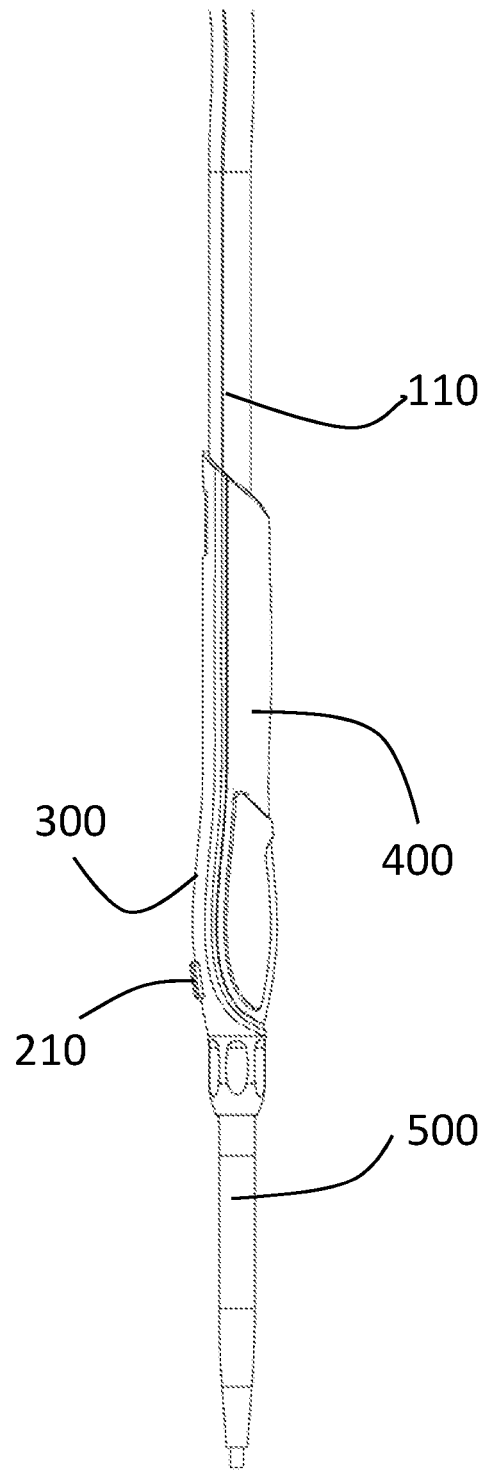
FIG. 2C is a first side view of a cold plasma scalpel and electrosurgical hand piece in accordance with a preferred embodiment of the present invention.
Figure 2D:
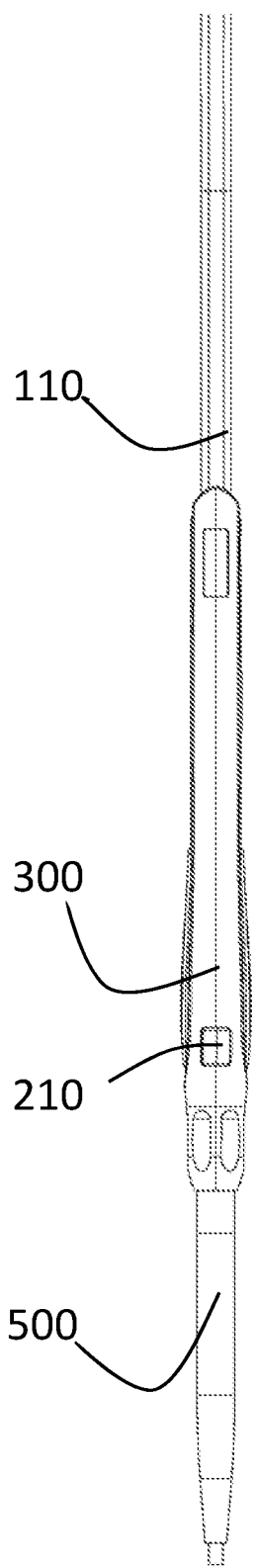
FIG. 2D is a top view of a cold plasma scalpel and electrosurgical hand piece in accordance with a preferred embodiment of the present invention.
Figure 2E:
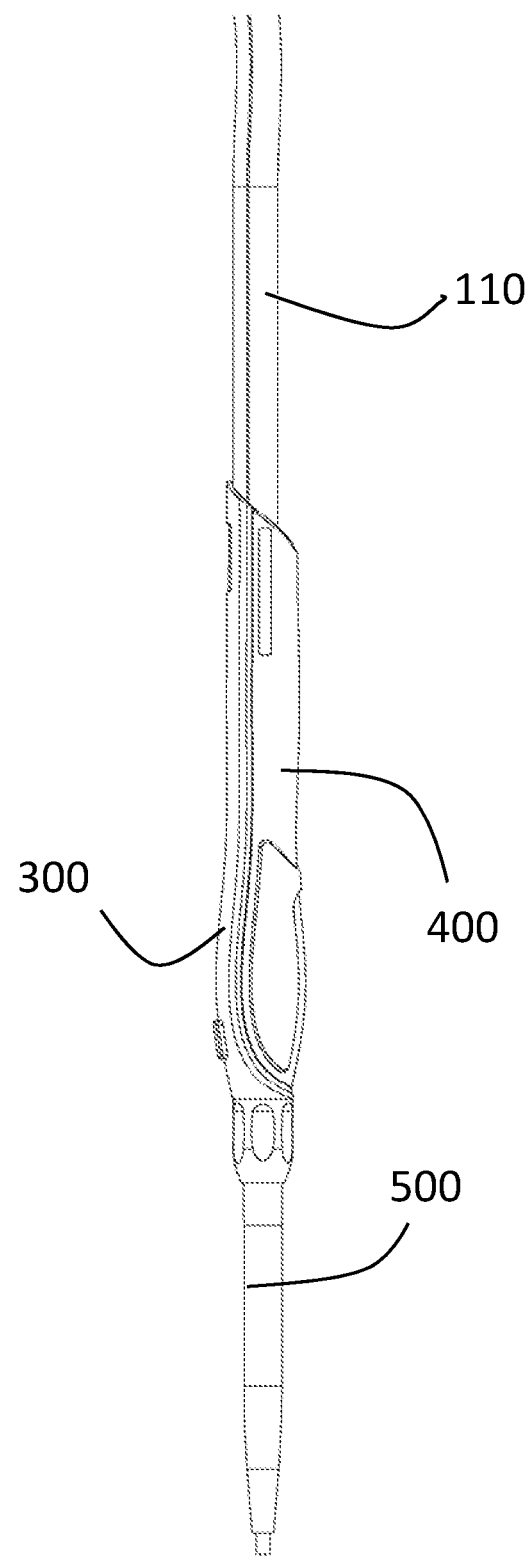
FIG. 2E is a second side view of a cold plasma scalpel and electrosurgical hand piece in accordance with a preferred embodiment of the present invention.
Figure 3A:
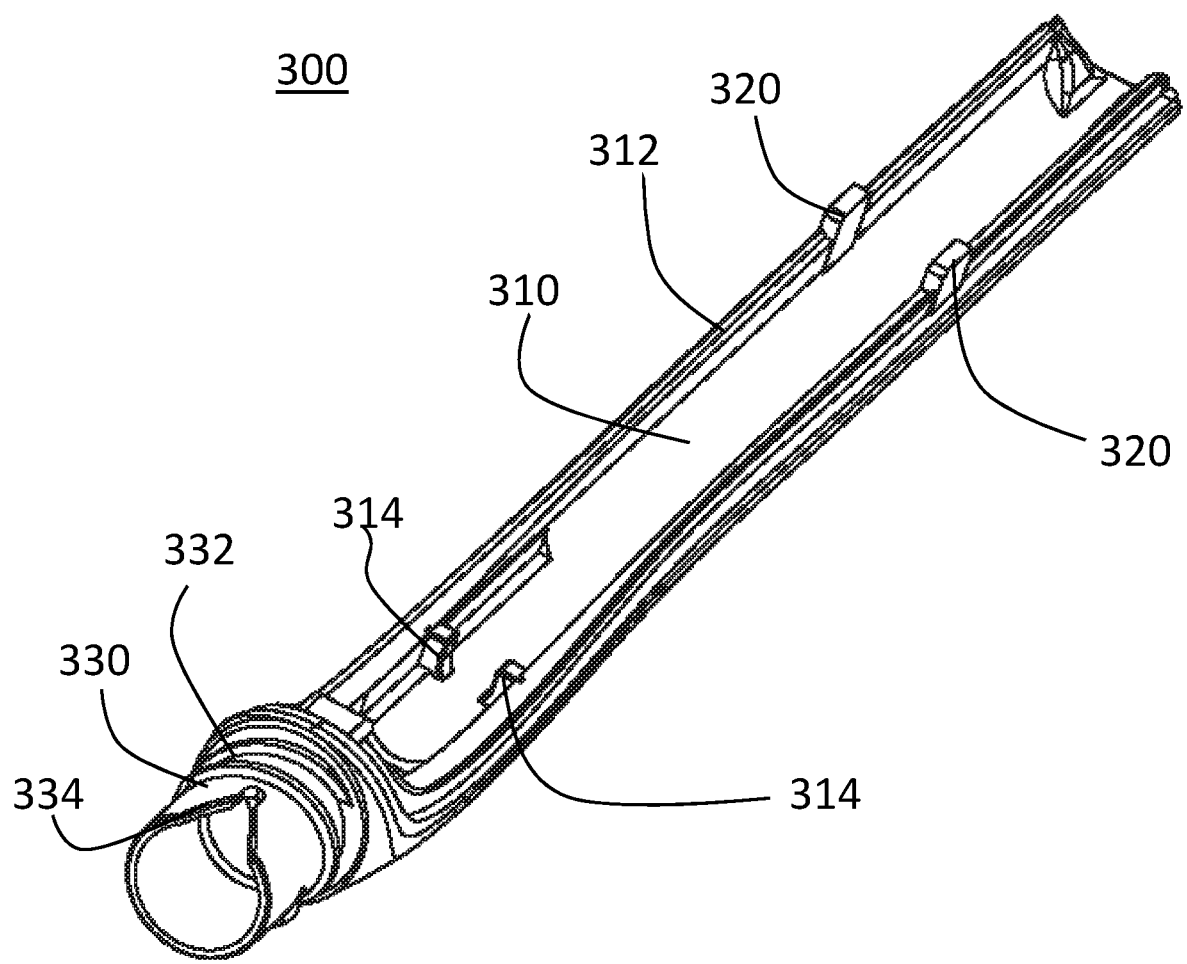
FIG. 3A is a front perspective view of a top hand piece portion of cold plasma scalpel hand piece in accordance with a preferred embodiment of the present invention.
Figure 3B:
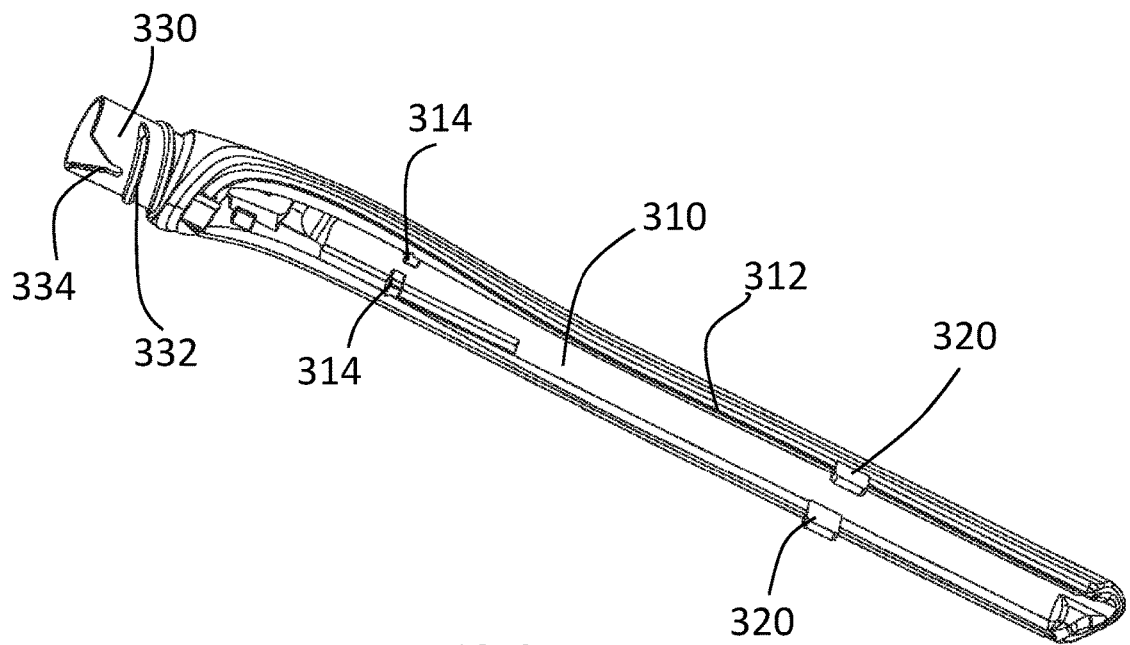
FIG. 3B is a bottom perspective view of a top hand piece portion of cold plasma scalpel hand piece in accordance with a preferred embodiment of the present invention.
Figure 3C:
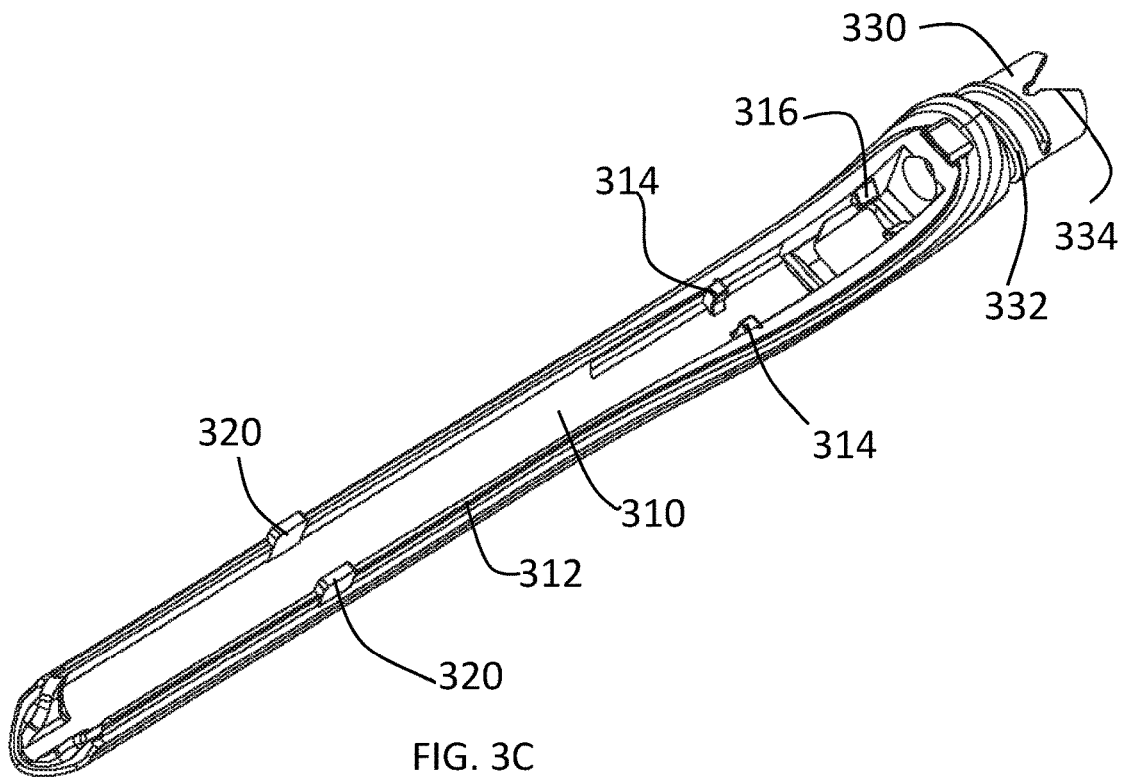
FIG. 3C is a top perspective view of a top hand piece portion of cold plasma scalpel hand piece in accordance with a preferred embodiment of the present invention.
Figure 5A:
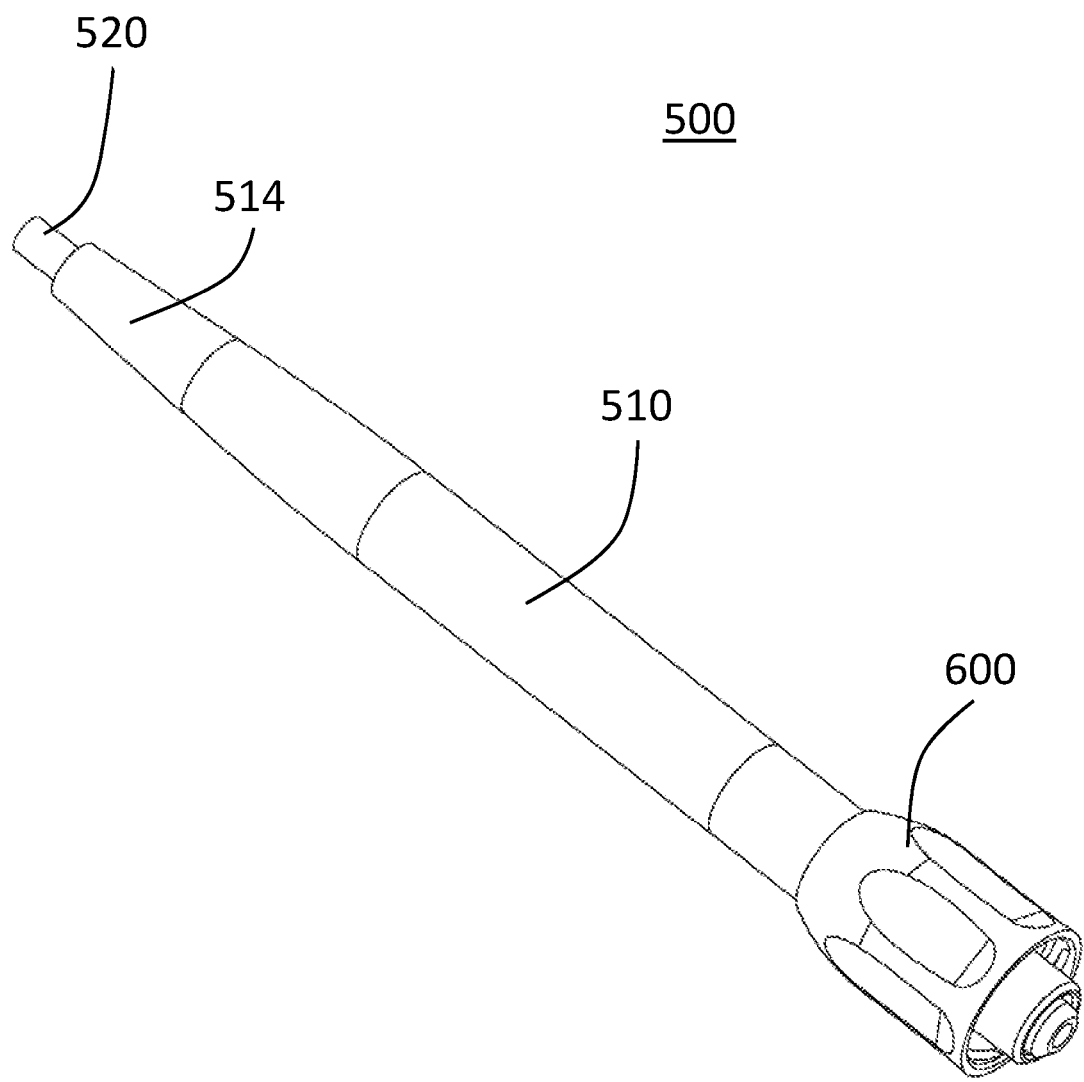
FIG. 5A is a perspective view of a cold plasma scalpel in accordance with a preferred embodiment of the present invention.
Figure 5B:
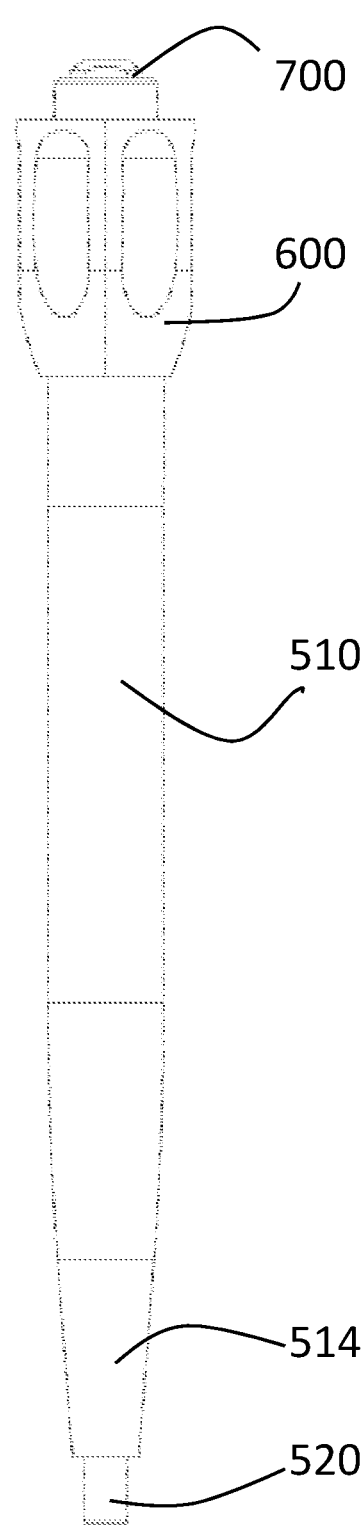
FIG. 5B is a first side view of a cold plasma scalpel in accordance with a preferred embodiment of the present invention.
Figure 5C:
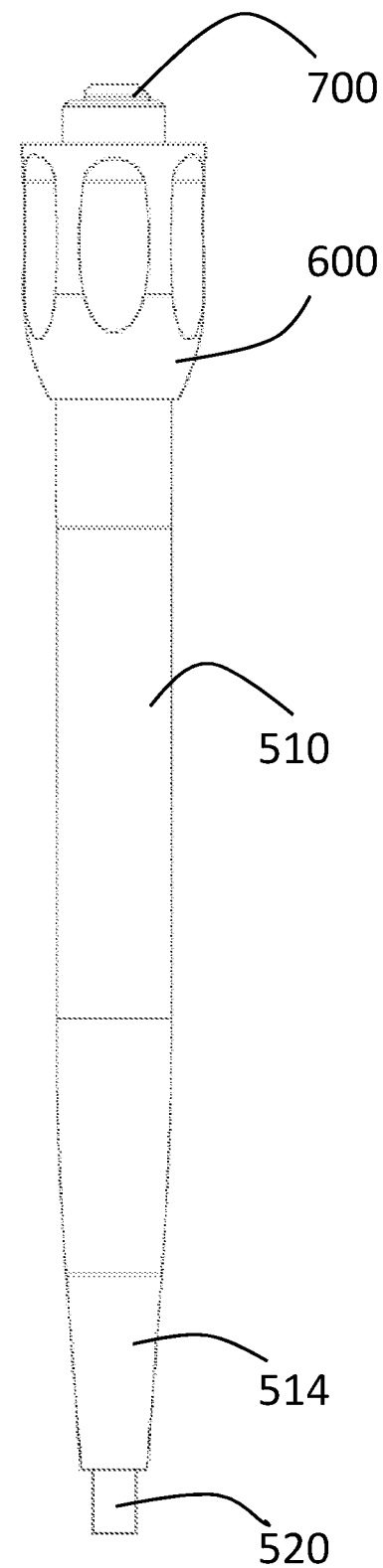
FIG. 5C is a second side view of a cold plasma scalpel in accordance with a preferred embodiment of the present invention.

A preferred embodiment of a cold plasma scalpel according to the present invention is described with reference to the figures. A hand piece assembly 200 has a top side piece 300 and a bottom side piece 400. A control button 210 extends from the interior of the hand piece through an opening in the top side piece 300. Within the hand piece is body connector funnel 806, PCB board 808, electrical wiring 120 and hose tubing (PVC medical grade) 140. The wiring 120 and hose tubing 140 are connected to one another to form a wire and tubing bundle 110. A grip over mold 820 extends over the bottom piece portion 400. In other embodiments, a grip may be attached to the bottom piece 400 in other manners. A probe or scalpel assembly 500 is attached to the end of the hand piece. The scalpel assembly 500 has non-bendable telescoping tubing 510, a ceramic tip 520, a column nut or collet 600 and body connector tubing 802. The hose tubing 140 extends out of the proximal end of the hand piece to a body gas connector 150, which has an O-ring 152, gas connector core 154 and gas connector tip 156 for connecting to a source of gas (not shown). The printed circuit board 808 connects to electrical wiring 120 which leads to electrical connector 130 having electrical pins 132.

Figure 6A:
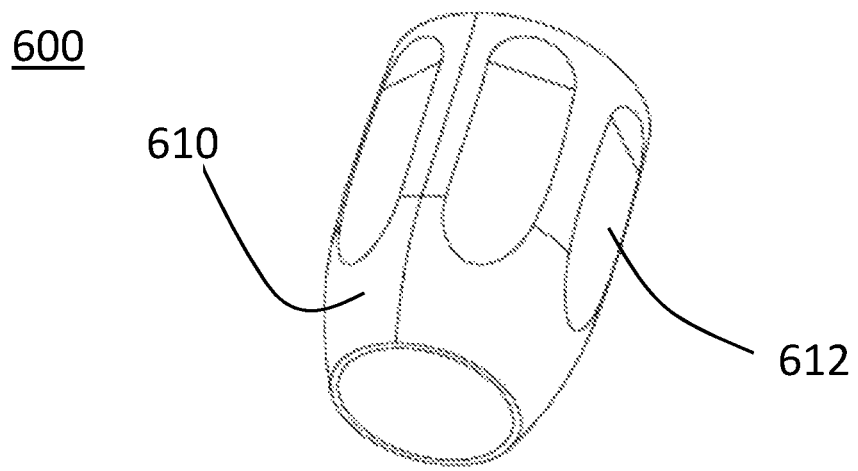
FIG. 6A is a bottom perspective view of an accessory locking nut or collet of a cold plasma scalpel in accordance with a preferred embodiment of the present invention.
Figure 6B:
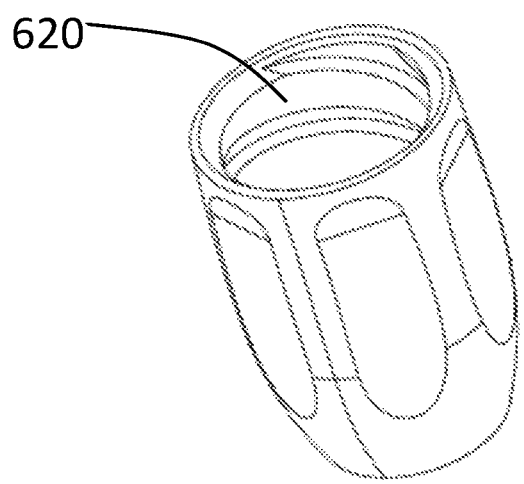
FIG. 6B is a top perspective view of an accessory locking nut or collet of a cold plasma scalpel in accordance with a preferred embodiment of the present invention.
Figure 7A:
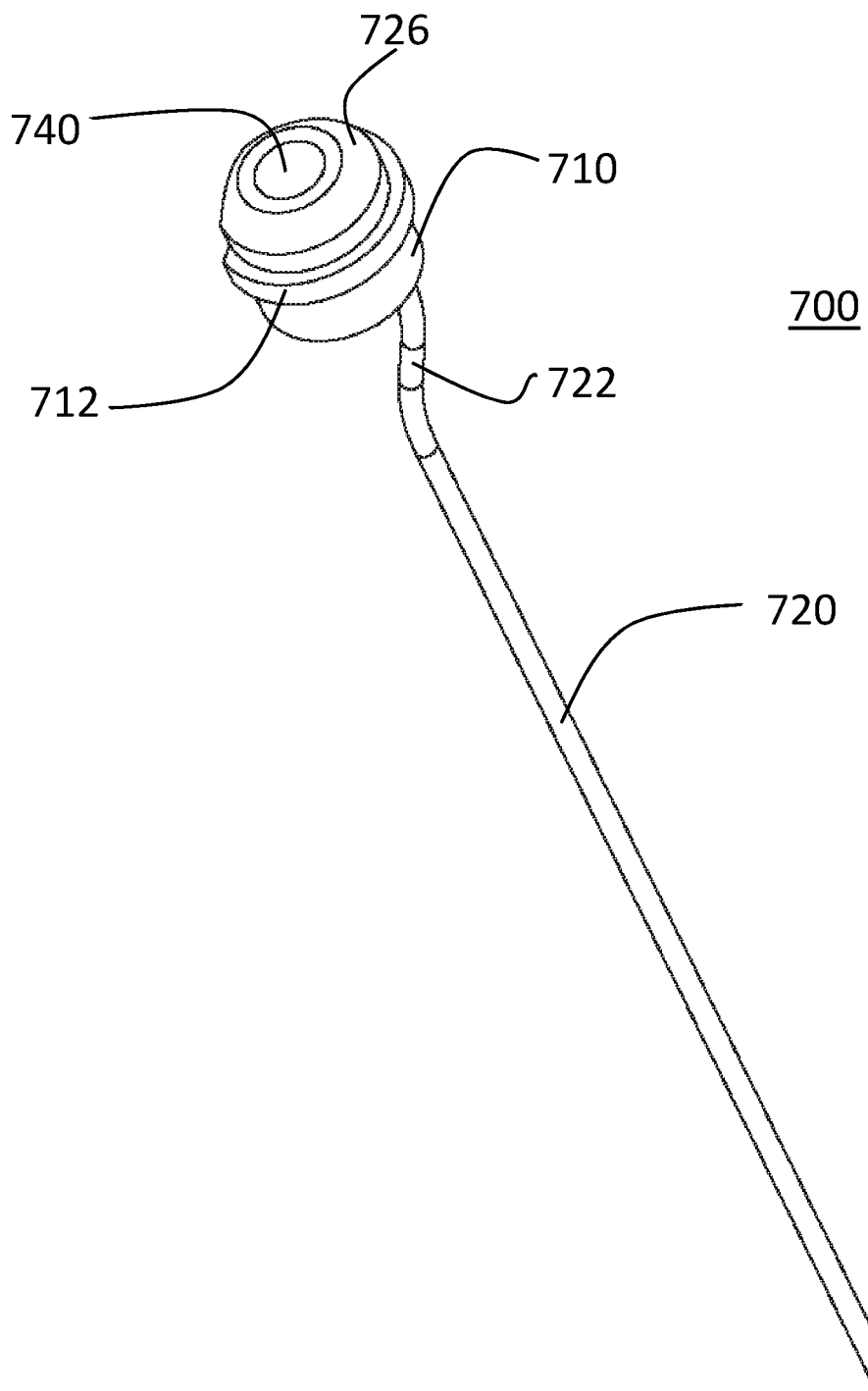
FIG. 7A is a top perspective view of an electrode of a cold plasma scalpel in accordance with a preferred embodiment of the present invention.
Figure 7B:
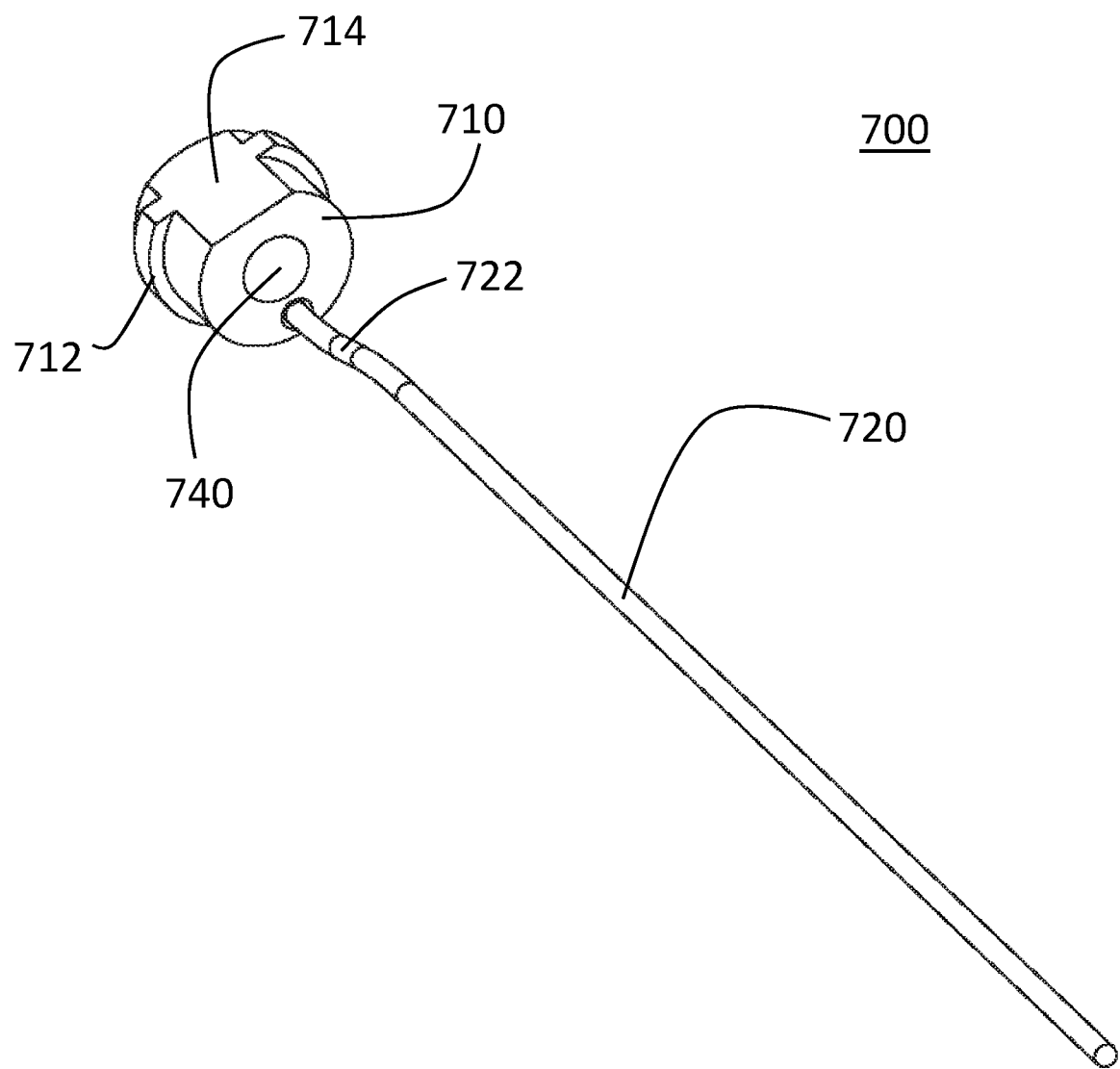
FIG. 7B is a bottom perspective view of an electrode of a cold plasma scalpel in accordance with a preferred embodiment of the present invention.
Figure 7G:
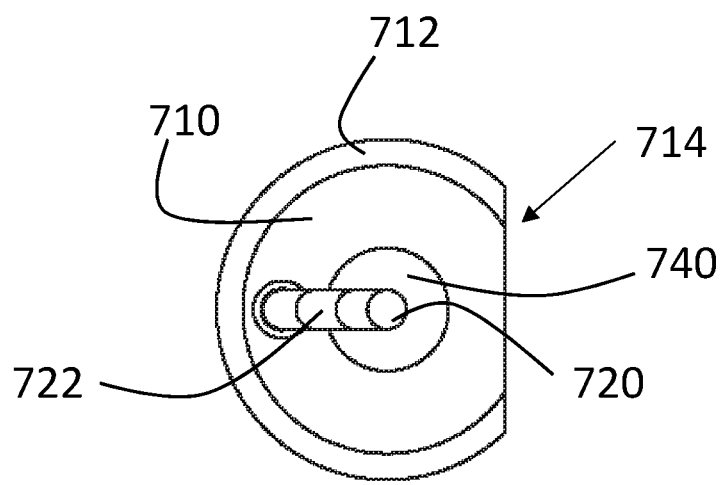
FIG. 7G is a first end view of an electrode of a cold plasma scalpel in accordance with a preferred embodiment of the present invention.
Figure 7H:
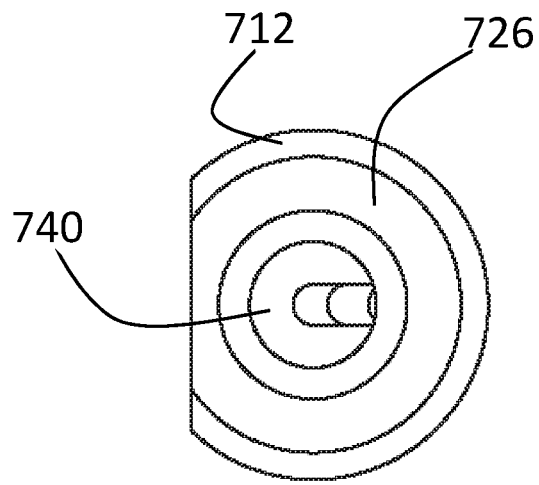
FIG. 7H is a second end view of an electrode of a cold plasma scalpel in accordance with a preferred embodiment of the present invention.
Figure 8:
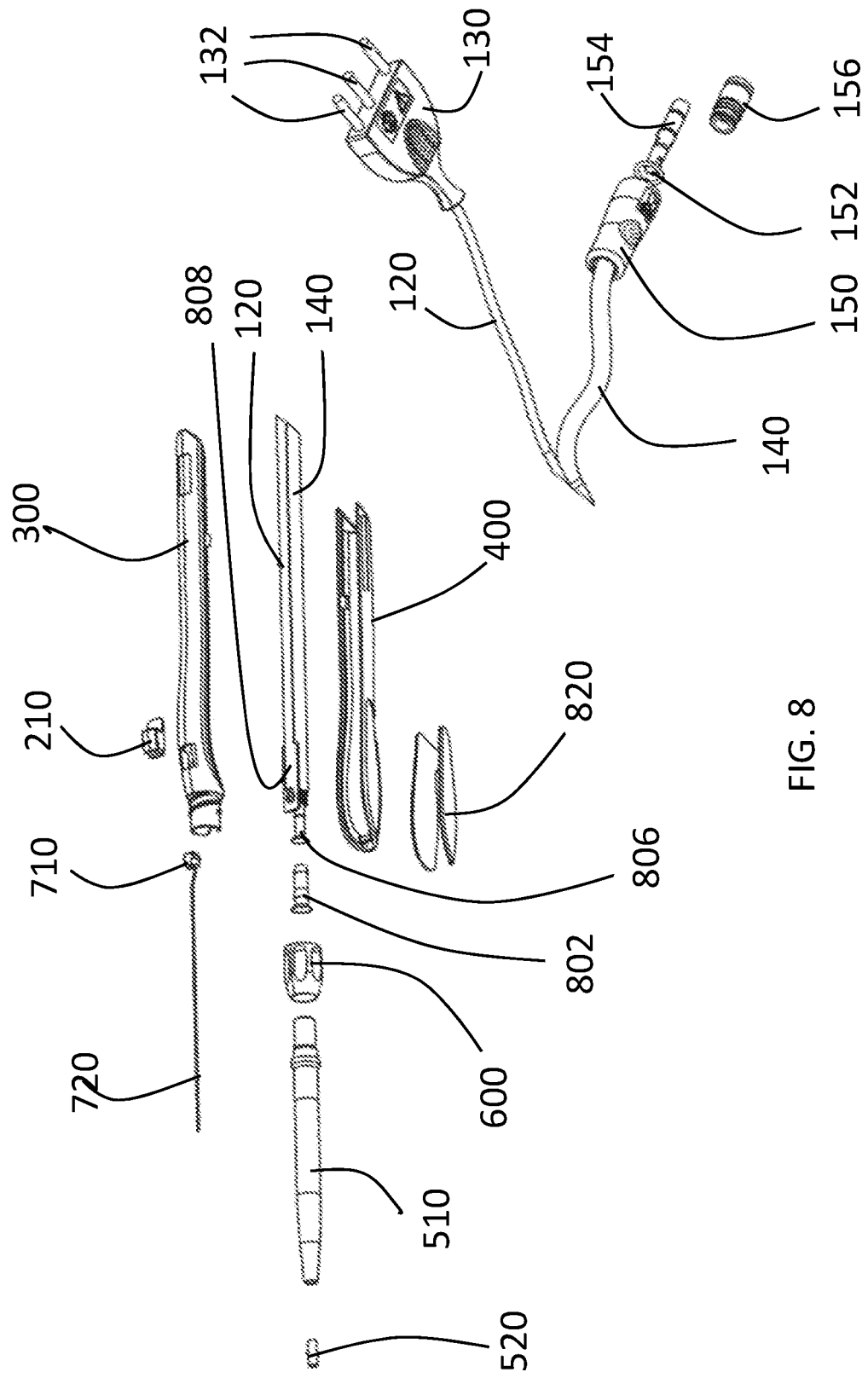
FIG. 8 is an assembly view of a cold plasma scalpel in accordance with a preferred embodiment of the present invention.

The collet 600, show in in FIGS. 6A-6B, has a body 610 having a plurality of depressions or dimples 612 on its exterior for gripping the collet. The interior of the collet 600 has threads 620 for engaging with threads on the hand piece 200.

The hand piece 200 has a housing having an upper portion 300 shown in FIGS. 3A-3F and a lower portion shown in FIGS. 4A-4C. The upper portion has a body 310 having an opening 319 for receiving a control button. Although only one opening 319 is shown in this embodiment, other embodiments with additional openings for additional control buttons will be apparent to those of skill in the art. The upper portion 300 has a ridge structure 312 along its sides and tabs 320 for mating with the bottom portion 400. The upper portion 300 has a neck 330 having threads 332 for mating with the threads 620 on the collet 600. The neck additionally may have a self-alignment feature 334. On the interior of the upper portion 300 adjacent the hole is a pair of support elements 316 for supporting PCB board 808 and control button 210 for controlling gas flow and/or electricity. Additional support elements 314 support the PCB board. A foot pedal or pedals may be used in addition or instead of bottom 210 to control gas flow and/or electricity. The bottom portion 400 of the hand piece 200 has a body 410 a pair of grip portions 440 or a grip over mold 820, grooves 420 for engaging with tabs 320 in the upper portion 300, and a ridge structure 412 for engaging with the ridge structure 312 in the upper portion 300 of the hand piece 200, and a slot 450 for engaging with tab 318 in the top piece.

The cold plasma scalpel assembly 500 is described in more detail with reference to FIGS. 5A-7H. As discussed previously, the scalpel assembly 500 has a housing or body 510 having a channel within it, a ceramic tip 520, a column nut or collet 600. The housing 510 has a tapered portion 514 near its distal end, an outer shoulder 512 and a pair of inner shoulders 521 and 522. The housing or body 510 may be telescoping and may be comprised of telescoping tubing. The housing or body 510 has a proximal end that connects to the hand piece 200 by means of collet 600 and a distal end extending away from the hand piece 200. Within the proximal end of the housing or body 510 is a lip, flange or other support member 522 for receiving an electrode connector. The telescoping tubing 510 may be of any length from a few millimeters to tens of centimeters or longer. Near the distal end of the housing 510 is a constrictor 530 having within it an obstruction 532 that provides for increased flow velocity of a gas flowing through the attachment when in use.

An electrode 700 is inserted into the distal end of the tubing, housing or body 510. The electrode has a connector and a wire or elongated portion. The connector and wire may be formed from the same or different materials. For example, the connector may be nickel-plated brass and the wire tungsten. The connector is at the proximal end of the electrode and has a connector body 710 having a beveled or rounded distal end and a proximal end. The connector may generally be cylindrical in shape but may have a flat portion 714 for alignment of the electrode in the housing 510. The body 710 has a channel 740 extending through it and a ridge, shoulder or flange 712. The wire 720 of the electrode is connected to the distal end of the connector adjacent the opening 740 and extends from the distal end of the connector. The wire 720 has a bent portion 722.

When the attachment 500 is fully assembled, the wire 720 extends down approximately the center of the channel in the housing 510 to a position near or extending from the distal end of the housing 510 and the ceramic tip 520. The distal face of the connector body 710 rests on shoulder 520 in housing 510 and the electrode shoulder 712 rests on the shoulder 522 of housing 510. The rounded or beveled portion 726 of the connector provides a conductive surface for making a connection to connector 802.

During use, an inert gas such as helium or argon flows from a gas source, through the hand piece and into the channel within the housing 510. The gas flows through the opening 740 in the connector body 710 and down the channel in the housing 510. The gas flowing down the channel in the housing 510 surrounds the wire 720. Electrical energy is supplied from an electrosurgical generator and flows through connector 130 to wire 120, through the hand piece and various connectors to the electrode 700. As the gas flows through the attachment, the electrode connector 710 and the wire 720 highly ionize the gas so the gas becomes a cold plasma. The system is monopolar, so the attachment and hand piece include only the active electrode 700. A conductive plate may be placed under the patient and acts as the return electrode or ground.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A device for performing cold atmospheric plasma treatment on a patient comprising:
    a hand piece having an inner cavity, said hand piece having a proximal end and a distal end;
    flexible tubing within said cavity and extending from said proximal end of said hand piece;
    wiring within said cavity and extending from said proximal end of said hand piece;
    a printed circuit board within said cavity and connected to said wiring;
    a conductive connector tube electrically connected to said printed circuit board, said conductive connector tube having an inner channel connected to a distal end of said flexible tubing;
    a rigid tube extending away from said distal end of said hand piece, said rigid tube having an interior channel;
    an electrode within said rigid tube, wherein said electrode comprises:
        a conductive connector having a contact surface contacting said conductive connector tube, a distal end surface facing away from said conductive connector tube, and a channel extending through a center of said conductive connector, said channel being fluidly connected to said flexible tubing, said distal end surface of said conductive connector being outside of said channel in said conductive connector and facing said interior channel of said rigid tube; and
        a conductive wire connected to said distal end surface of said conductive connector;
        wherein said conductive wire extends substantially along the length of the rigid tubing.

2. A device for performing cold atmospheric plasma treatment on a patient according to claim 1 further comprising:

an insulating tip at a distal end of said rigid tube; wherein said conductive wire extends at least partially through said insulating tip.

3. A device for performing cold atmospheric plasma treatment on a patient according to claim 1 wherein said conductive connector comprises a nickel plated brass alloy.

4. A device for performing cold atmospheric plasma treatment on a patient according to claim 1 wherein said hand piece further comprises a grip material overmolded onto an exterior of said hand piece, wherein said hand piece is comprised of a first material and said grip material is comprised of a second material different than aid first material.

5. A device for performing cold atmospheric plasma treatment on a patient according to claim 1 wherein said hand piece has a plurality of support elements within the inner cavity for supporting said printed circuit board within said hand piece.

6. A device for performing cold atmospheric plasma treatment on a patient according to claim 1 wherein said tubing and said wiring within said inner cavity of said hand piece are connected together to form a bundle.

7. A device for performing cold atmospheric plasma treatment on a patient according to claim 1, further comprising a connector funnel for fluidly connecting said flexible tubing to said conductive connector tube.

\* \* \* \* \*